United States Patent
Sawyer

[11] Patent Number: 5,569,764
[45] Date of Patent: Oct. 29, 1996

[54] N-BENZYL DIHYDROINDOLE $LTD_4$ ANTAGONISTS

[75] Inventor: J. Scott Sawyer, Indianapolis, Ind.

[73] Assignee: Eli Lilly and Company, Indianapolis, Ind.

[21] Appl. No.: 414,269

[22] Filed: Mar. 31, 1995

Related U.S. Application Data

[62] Division of Ser. No. 166,489, Dec. 14, 1993, Pat. No. 5,486,612.

[51] Int. Cl.$^6$ .............. C07D 401/14; C07D 409/14; A61K 31/425; A61K 31/44
[52] U.S. Cl. .............. 546/268.4; 546/277.4; 546/277.7; 548/181
[58] Field of Search .............. 546/283, 276; 548/181; 514/365, 340

[56] References Cited

FOREIGN PATENT DOCUMENTS 0 469 833  7/1991  European Pat. Off. .

*Primary Examiner*—David B. Springer
*Attorney, Agent, or Firm*—Roger S. Benjamin; David E. Boone

[57] ABSTRACT

This invention relates to pharmaceutical N-benzyl dihydroindole compounds having the general formula:

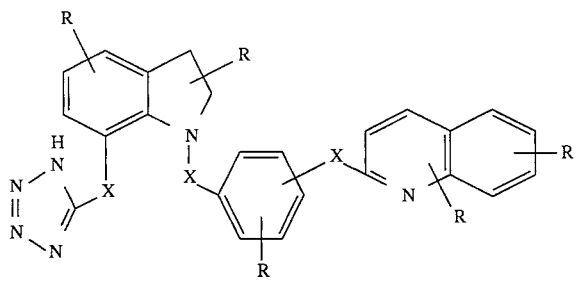

and their use as $LTD_4$ antagonists.

7 Claims, No Drawings

N-BENZYL DIHYDROINDOLE LTD$_4$ ANTAGONISTS

This application is a division of application Ser. No. 08/166,489, filed Dec. 14, 1993, U.S. Pat. No. 5,486,612.

FIELD OF THE INVENTION

This invention relates to pharmaceutical N-benzyl dihydroindole compounds, their use and preparation.

BACKGROUND OF THE INVENTION

European Patent Application 0469833 (published Feb. 5, 1992) describes various N-benzyl-indoles and their utility as LTD$_4$ antagonists.

It is a suprising discovery of this invention that hydrogenated indoles (dihydroindoles) have utility as LTD$_4$ antagonists together with increased bioavailability and solubility compared to prior art compounds.

SUMMARY OF THE INVENTION

The compounds of the invention are of the formula I

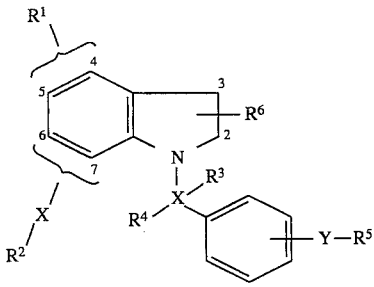

Another aspect of the invention are pharmaceutical formulations containing the novel compounds of formula (I).

Still another aspect of this invention is a method of treating an animal, including a human, for a disease in which leukotrienes are a causal mediator.

DETAILED DESCRIPTION OF THE INVENTION

The compounds of the invention are leukotriene antagonists.

The compounds of the invention are of the formula (I) and pharmaceutically acceptable salts thereof;

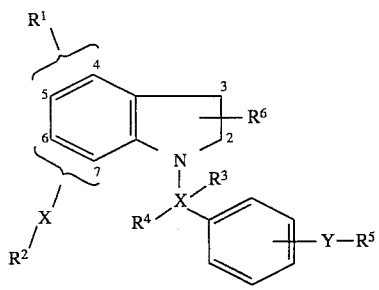

wherein $R^1$ is hydrogen, halo, $C_{1-4}$ alkyl, $C_{1-4}$ alkoxy, nitrile, optionally protected carboxy, optionally protected tetrazolyl, trihalomethyl, hydroxy-$C_{1-4}$ alkyl, aldehydo, —CH$_2$Z,— CH=CH—Z or —CH$_2$CH$_2$Z, where Z is optionally protected carboxy or optionally protected tetrazolyl;

$R^2$ is halo, nitrile, an optionally protected acid group, $C_{1-4}$ alkoxy-carbonyl, or —CONR$^7$R$^8$ where $R^7$ and $R^8$ are each hydrogen or $C_{1-4}$ alkyl;

$R^3$ and $R^4$ are each hydrogen, $C_{1-4}$ alkyl, optionally substituted phenyl, or $C_{1-4}$ alkyl substituted by —CONR$^7$R$^8$ or an optionally protected acid group;

$R^5$ is selected from the following four formulae:

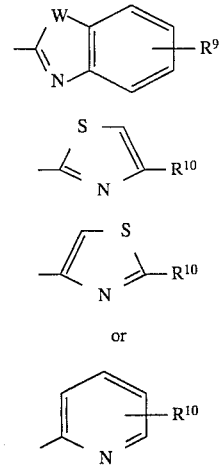

where

W is —CH=CH—, —CH=N—, —N=CH—, —O— or —S—, $R^9$ is hydrogen, halo, $C_{1-4}$ alkyl, $C_{1-4}$ alkoxy or trihalomethyl, and $R^{10}$ is hydrogen, $C_{1-4}$ alkyl, $C_{2-6}$ alkenyl, $C_{3-6}$ cycloalkyl or $C_{1-4}$ alkyl-$C_{3-6}$ cycloalkyl; $R^6$ is hydrogen or $C_{1-4}$ alkyl;

each X is independently selected from, —O—(CH$_2$)$_n$CR$^{11}$R$^{12}$—, —S— (CH$_2$)$_n$—CR$^{11}$R$^{12}$—, —CR$^{11}$R$^{12}$—, —CR$^{11}$R$^{12}$—(CH$_2$)$_n$—CR$^{13}$R$^{14}$— or —CR$^{11}$=CR$^{12}$—, where $R^{11}$,$R^{12}$,$R^{13}$ and $R^{14}$ are each hydrogen or $C_{1-4}$ alkyl;

n is 0, 1 or 2; and

Y is —O—CR$^{15}$R$^{16}$—, —S—CR$^{15}$R$^{16}$—, —CR$^{15}$=CR$^{16}$ — or —CR$^{15}$R$^{16}$—CR$^{17}$R$^{18}$— where $R^{15}$, $R^{16}$, $R^{17}$ and $R^{18}$ are each hydrogen or $C_{1-4}$ alkyl.

In the above formula (I), a halo substituent can be for example, chloro, bromo and fluoro and is preferably chloro. A $C_{1-4}$ alkyl group includes methyl, ethyl, propyl, isopropyl, butyl and tert-butyl and is preferably methyl or ethyl, and a $C_{1-4}$ alkoxy group is one such alkyl group attached through oxygen. A hydroxy-$C_{1-4}$ alkyl group is a hydroxy-substituted $C_{1-4}$ alkyl group preferably of the formula HO(CH$_2$)$_n$— where n is 1 to 4, a preferred group being hydroxymethyl. A $C_{3-6}$ cycloalkyl group includes, for example, cyclopropyl, cyclopentyl and cyclohexyl, and is preferably cyclopropyl. The $C_{3-6}$ cycloalkyl group can be substituted by a $C_{1-4}$ alkyl. A $C_{2-6}$ alkenyl group is preferably propenyl or isopropenyl. A trihalomethyl group is preferably trifluoromethyl. An optionally substituted phenyl group is phenyl itself, or phenyl substituted with one or more, preferably 1 to 3, substituents selected from $C_{1-4}$ alkyl, especially methyl, $C_{1-4}$ alkoxy, especially methoxy and ethoxy, hydroxy, nitro, cyano, halo, especially chloro or fluoro, trihalomethyl, especially trifluoromethyl, carboxy, $C_{1-4}$ alkoxy-carbonyl, and optionally protected tetrazolyl.

An acid group can be any acid group conventionally used in pharmaceutical chemistry and the term includes, for example, tetrazolyl (1H-tetrazol-5-yl), carboxy (—COOH), phosphonate (—PO(OH)$_2$), sulphonate (—SO$_2$OH), acyl sulphonamido (—CONHSO$_2$R), where R is preferably $C_{1-4}$ alkyl or optionally substituted phenyl or cyanoguanidinyl (—NHC(NH$_2$)=NCN). Especially preferred examples are tetrazolyl and carboxy.

When R$^5$ is the group

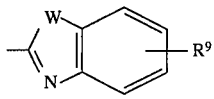

it comprises groups of the following type

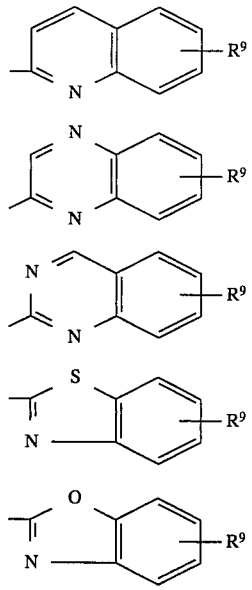

and the quinolin-2-yl group is the most preferred.

The value of R$^1$ is preferably hydrogen or halogen, and especially hydrogen, and when it is other than hydrogen it is preferably attached to the indole nucleus at the 4-position.

The group R$^2$—X— is attached to the indole nucleus at the 6- or 7-position, and when X is —O—(CH$_2$)$_n$—CR$^{11}$R$^{12}$— via the oxygen atom. R$^2$ is preferably an acid group especially tetrazolyl or carboxy.

The groups R$^3$ and R$^4$ can be hydrogen C$_{1-14}$ alkyl or optionally substituted phenyl, and preferred instances are those in which R$^3$ and R$^4$ are both hydrogen, R$^3$ is hydrogen and R$^4$ is C$_{1-4}$ alkyl or optionally substituted phenyl, and R3 and R4 are each C$_{1-4}$ alkyl, preferably methyl or ethyl. A further preferred instance is one in which R$^3$ is C$_{1-4}$ alkyl substituted by an acid group and R$^4$ is hydrogen or C$_{1-4}$ alkyl.

The R$^5$ group is preferably quinolin-2-yl where the substituent R$^9$, which is preferably hydrogen or halo, is attached at the 7-position. The group R$^5$—Y— can be attached at the 2—, 3- or 4-positions to the phenyl nucleus, and when Y is —O—CR$^{15}$R$^{16}$— via the oxygen atom. R$^5$—Y— is preferably attached at the 3- or 4-positions.

The R$^6$ group is preferably hydrogen and when it is C$_{1-4}$ alkyl is preferably attached at the 3-position.

The linking group X is preferably —O—CR$^{11}$R$^{12}$— or CR$^{11}$R$^{12}$—CR$^{13}$R$^{14}$—, and R$^{11}$, R$^{12}$, R$^{13}$ and R$^{14}$ are preferably hydrogen. Linking group Y is preferably of the formula —O—CR$^{15}$R$^{16}$— or —CR$^{15}$=CR$^{16}$—, and R$^{15}$, R$^{16}$, R$^{17}$ and R$^{18}$ are preferably hydrogen.

A subset of compounds of the invention having 7 position substitution of the —X—R$^2$ substituent are represented by the formula (II):

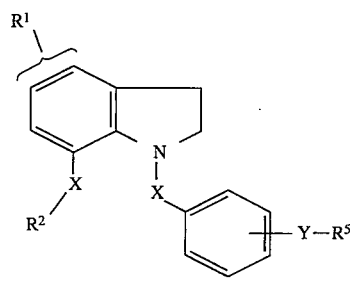

in which R$^1$ is hydrogen, halo, C$_{1-4}$ alkyl, C$_{1-4}$ alkoxy, nitrile, optionally protected carboxy, C$_{1-4}$ alkoxy-carbonyl or trihalomethyl; R$^2$ is tetrazolyl, nitrile, carboxy, C$_{1-4}$ alkoxy-carbonyl or —CONR$^7$R$^8$ where R$^7$ and R$^8$ are each hydrogen or C$_{1-4}$ alkyl; R$^5$ is

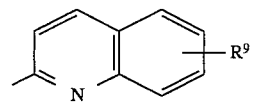

where R$^9$ is hydrogen, halo, C$_{1-4}$ alkyl, C$_{1-4}$ alkoxy or trihalomethyl; each X is independently selected from a bond, —(CH$_2$)$_n$— where n is from 1 to 5, —O—CR$^{11}$R$^{12}$—, —CR$^{11}$R$^{12}$—CR$^{13}$R$^{14}$ or —CR$^{11}$=CR$^{12}$— where R$^{11}$, R$^{12}$, R$^{13}$ and R$^{14}$ are each hydrogen or C$_{1-4}$ alkyl; and Y is —O—CR$^{15}$R$^{16}$— or —CR$^{15}$=CR$^{16}$— where R$^{15}$ and R$^{16}$ are each hydrogen or C$_{1-4}$ alkyl; and salts thereof.

Another preferred group of compounds of the invention are defined by formula (II) where R$^1$ is hydrogen or halo, R$^2$X— is tetrazolyl-CH$_2$O— or tetrazolyl-CH$_2$CH$_2$—, and —Y— is

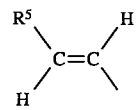

where R$^5$ is

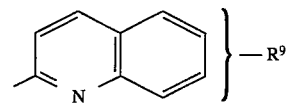

and R$^9$ is hydrogen or halo, and those in which R$^1$ is hydrogen or halo, R$^2$X— is tetrazolyl-CH$_2$— and —Y— is

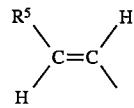

is where R$^5$ is

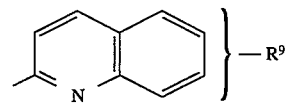

and R$^9$ is hydrogen or halo; the groups R$^1$ and R$^9$ being in the 4- or 5-positions and 6- or 7-positions, respectively.

Particularly preferred are 7-tetrazolyl and N-phenylene-quinolin-2-yl substituted compounds of the invention represented by the formula (III) as set out below:

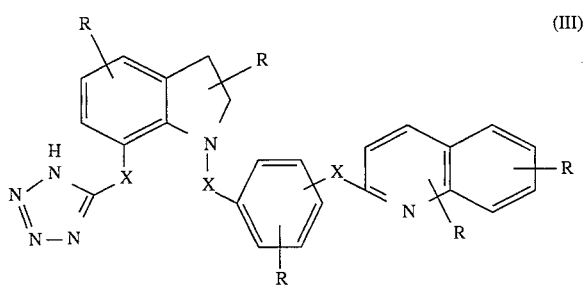

(III)

wherein;

each X is independently selected from —O—(CH$_2$)$_n$— or —(CH$_2$)$_n$—, —S—(CH$_2$)$_n$—, and trans-CH=CH—;

n is an integer from 0 to 3; and

R is independently selected from H, halo, and C$_{1-4}$ alkyl.

When acid substituents on the compound of formula (I) require protection during preparation they may be protected by conventional protecting groups. Such protected compounds are included in the scope of the invention, though the preferred compounds with optimum biological properties are the unprotected compounds derived from them. A carboxy can be protected by protecting groups which include the well known ester forming groups used for the temporary protection of acidic carboxylic acid groups.

Examples of protecting groups which have general use are readily hydrolysable groups such as arylmethyl groups, haloalkyl groups, trialkylsilyl groups, alkyl groups, and alkenyl groups. A preferred protected carboxy is C$_{1-4}$ alkoxy-carbonyl. Other carboxy protecting groups are described in the text, *Protective Groups in Organic Synthesis* by T. W. Greene and P. G. M. Wuts; publ. John Wiley & Sons Inc. New York 1991, ISBN 0-471-62301-6. Such protecting groups are also suitable for protecting phosphonate and sulphonate substituents. Furthermore, it is usually necessary to protect any metrazolyl group during the process of preparation, and suitable and well known protecting groups for this purpose include groups of the formula —CR'R"R'" where R' and R" are hydrogen, C$_{1-4}$ alkyl or phenyl optionally substituted by one or more electron-donating group such as for example, C$_{-4}$ alkoxy, and R'" is phenyl optionally substituted by one or more electron donating groups. Preferred examples include trityl and benzhydryl.

The invention comprises compounds of Formula (I) in unprotected form, and their pharmaceutically-acceptable salts for use in the treatment of diseases in which leukotrienes are a causal mediator.

Preferred individual compounds of the invention are illustrated by the following compounds A thru H, mixtures thereof, and their pharmaceutically acceptable salts:

Compound A

5-[2-[1-[3-[2-E-(7-Chloroquinolin-2-yl)ethenyl]
benzyl]-2,3-dihydroindol-7-yl]-ethyl]-1H-tetrazole

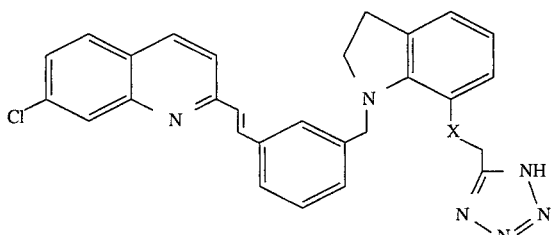

Compound B

5-[2-[1-[3-(7-Chloroquinolin-2-methoxy)benzyl]-
2,3-dihydroindol-7-yl]-ethyl]-1H-tetrazole

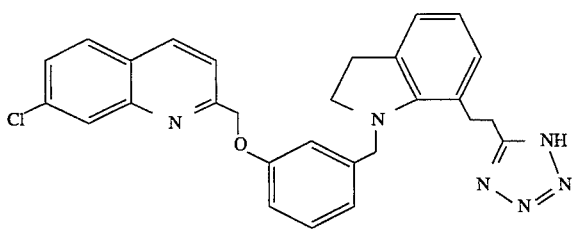

Compound C

5-[2-[1-[4-(7-Chloroquinolin-2-ylmethoxy)benzyl]-
2,3-dihydroindol-7-yl]-ethyl]-1H-tetrazole

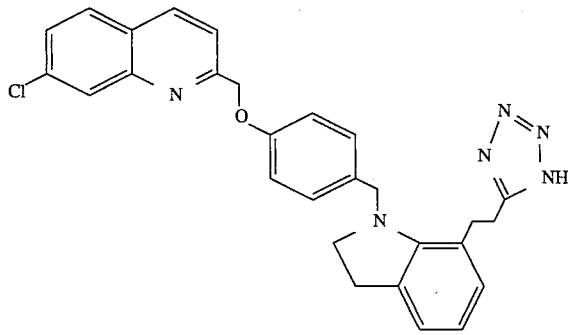

Compound D

5-[2-[2-[3-(Quinolin-2-ylmethoxy)benzyl]-
2,3-dihydroindol-7-yl]-ethyl]-1H-tetrazole

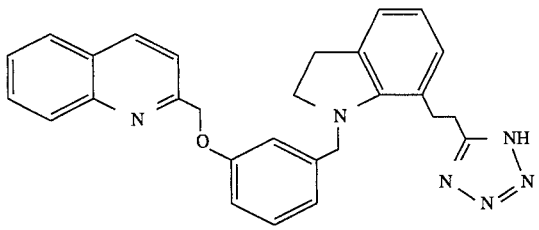

Compound E

5-[2-[1-[4-(Quinolin-2-ylmethoxy)benzyl]-2,3-dihydroindol-7-yl]-ethyl]-1H-tetrazole

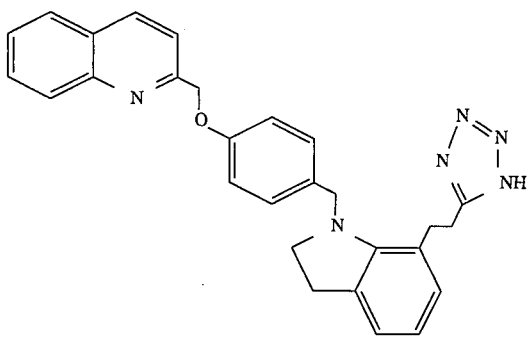

Compound F

5-[2-[1-[3-[2-E-(Quinolin-2-yl)ethenyl]benzyl]-2,3-dihydroindol-7-yl]ethyl]-1H-tetrazole

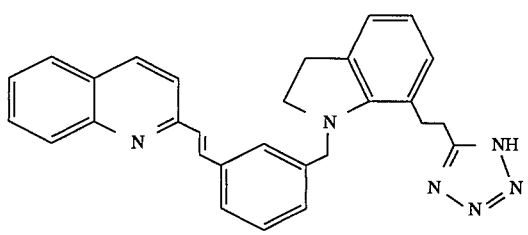

Compound G

5-[1-[3-[2-E-(7-Chloroquinolin-2-yl)ethenyl]benzyl]-2,3-dihydroindol-7-yloxymethyl]-1H-tetrazole

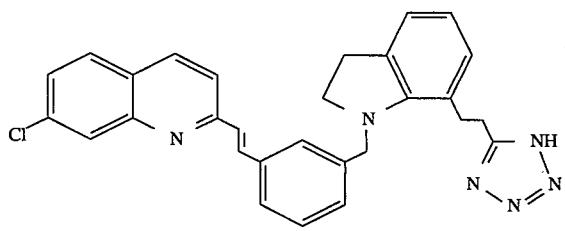

Compound H

5-[2-[1-[4-[2-E-(7-Chloroquinolin-2-yl)ethenyl]benzyl]-2,3-dihydroindol-7-yl]-ethyl]-1H-tetrazole

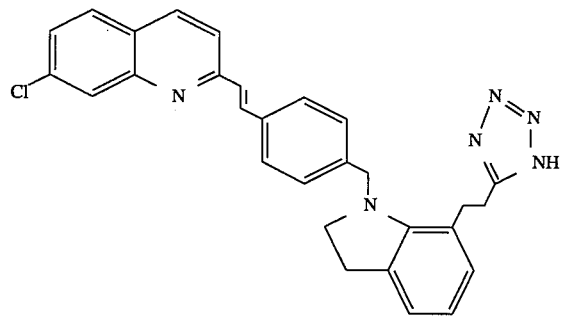

METHOD OF MAKING THE COMPOUNDS OF THE INVENTION

Process for producing a compound of the formula (I) are described as Methods (1), (2), (3), (4) (5) and (6) below:

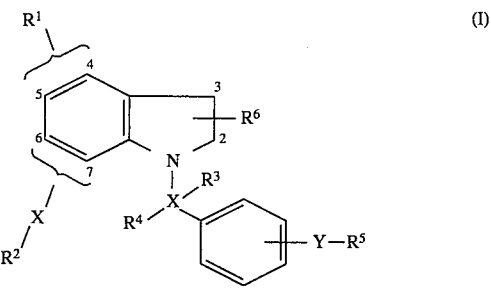

(I)

Method (1) reducing an indole of the formula (1a),

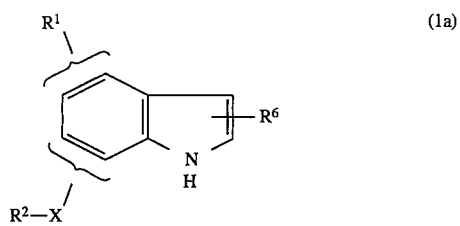

(1a)

then reacting the 2,3 dihydroindole product (1b)

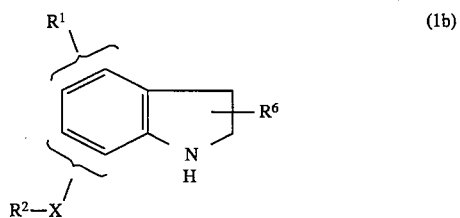

(1b)

with a compound of the formula

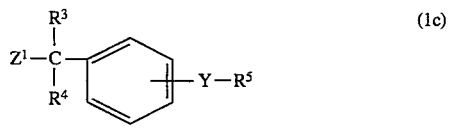

(1c)

where $Z^1$ is a leaving group;

Method (2) reducing an indole the formula (2a)

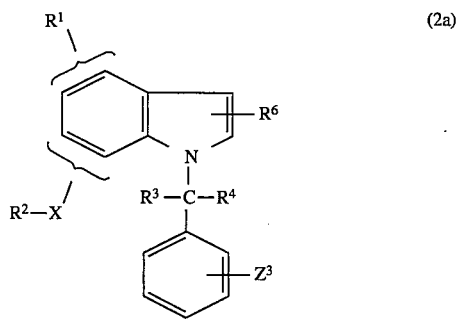

(2a)

then, reacting the 2,3 dihydroindole product (2b)

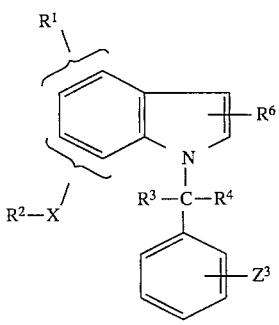
(2b)

with a compound selected from the formulae

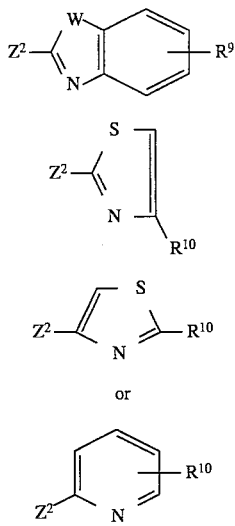

in which either $Z^3$ is —OH and $Z^2$ is —$CR^{15}R^{16}Z^1$ where $Z^1$ is a leaving group, or $Z^3$ is —$CR^{15}$=O and $Z^2$ is methyl or a Wittig-type moiety;

Method (3) reducing an indole the formula (3a)

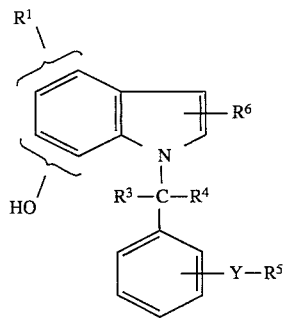
(3a)

then, alkylating the 2,3 dihydroindole product (3b)

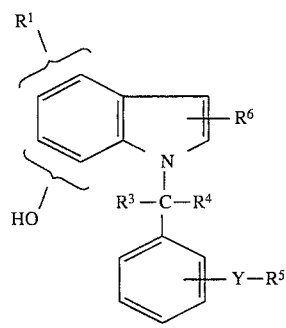
(3b)

with a compound of formula $R^2CR^{11}R^{12}(CH_2)_nZ^1$ where $Z^1$ is a leaving group, no give a compound of formula (I) in which X attached to the nitrogen is —O—$CH_2)_nCR^{11}R^{12}$—;

Method (4) reducing an indole the formula (4a)

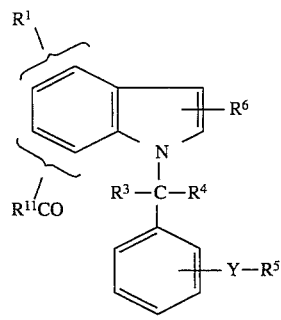
(4a)

then, reacting the 2,3 dihydroindole product (4b)

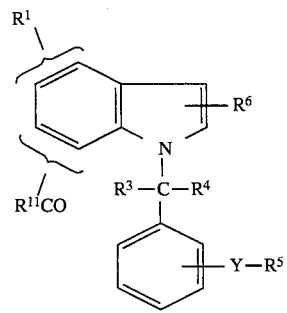
(4b)

with an isocyanide reagent or a Wittig-type reagent, to give a compound off formula (I) in which X attached to the nitrogen is —$CHR^{11}$— and $R^2$ is —CN or a compound in which X is —$CR^{11}$=$CR^{12}$; or Method (5) optionally, interconverting one or more of groups $R^1$, $R^2$, $R^3$ and $R^4$ of formula (I).

Method (6) The compounds of the invention may also be synthesized by reduction of N-Benzyl Indoles. Thus, N-benzyl indoles are reduced to give the N-benzyl dihydroindoles of the invention. Suitable N-benzyl indole starting materials and their preparation are disclosed in European Patent No. 0 469,833, the disclosure of which is incorporated herein by reference. Reduction of an N-benzyl indole is accomplished by use of sodium cyanoborohydride in acetic acid as shown below.

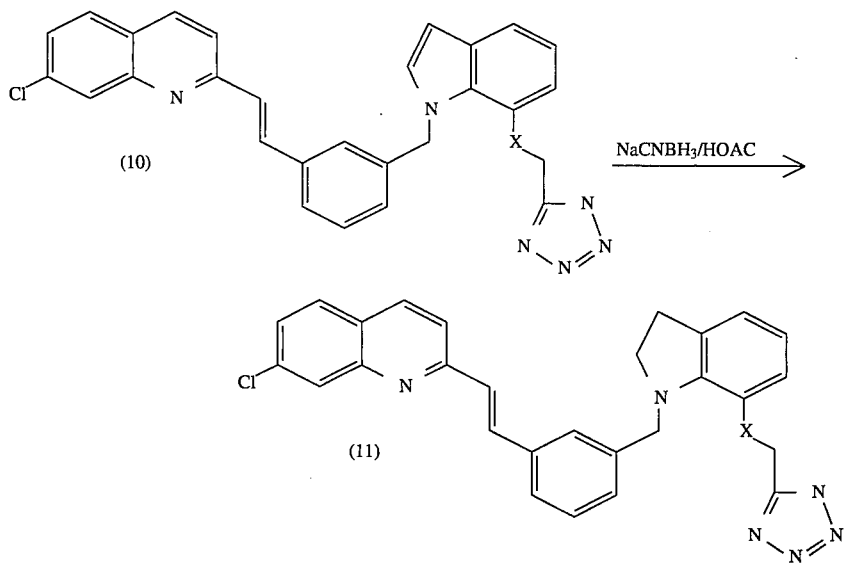

With regard to the above preparative methods for preparing the compounds of the invention, these are preferably carried out in the presence of an organic solvent and at a temperature of from 0° C. to 50° C. It is preferred to employ a base such as for example sodium hydride, sodium bis(trimethylsilyl) amide (prepared from 1,1,1,3,3,3-hexamethyl disilazane and an appropriate base) or potassium hydroxide. The leaving group, $Z^1$, is preferably halogen and in particular chloro. Other leaving groups such as tosylate or mesylate can, however, be employed. It will be appreciated that it may be necessary to protect any acid group during the process of preparation, and suitable and well known protecting groups for this purpose are described above. For example in the case of a tetrazolyl group protecting groups include trityl and benzhydryl formed by reaction with the appropriate halide in the presence of base, for example by reacting the tetrazolyl reactant with trityl chloride and triethylamine. Other acid groups such as carboxy, phosphonate and sulphonate can be protected by the formation of esters in conventional manner.

Intermediate compounds of formula (IV)

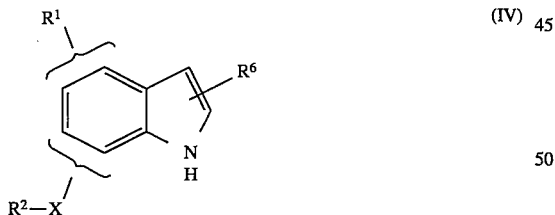

can conveniently be prepared by the following main routes. Firstly, if it is desired to prepare the compound in which X is $-O-(CH_2)_nCR^{11}R^{12}-$ attached via the oxygen to the 7-position on the phenyl nucleus, the starting point can be an appropriate ortho-nitrophenol which is first protected by, for example, benzylation, and reduced to give the aniline derivative. This can then be reacted with 2-methyl-thioacetaldehyde dimethyl acetal and the product cyclised by acid, as follows:

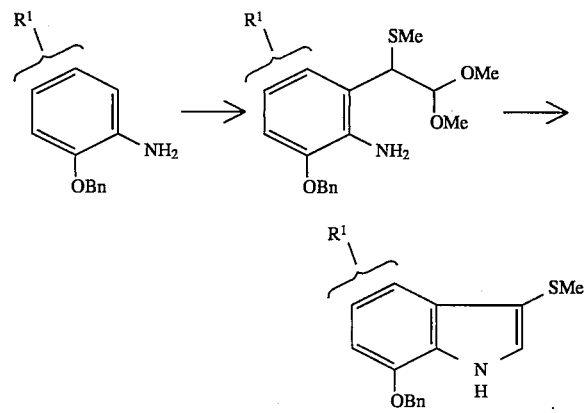

A preferred method of making indole intermediates with 7-oxy-substitution is by removing the methylthio substituent with Raney nickel and reducing with hydrogen and palladium to give an intermediate hydroxy-indole which, without necessarily being isolated, can be reacted in the presence of an appropriate base with suitable reagents of the formulae $Br(CH_2)_nCR^{11}R^{12}CN$ or $Br(CH_2)_nCR^{11}R^{12}CO_2R$, where R is $C_{1-4}$ alkyl, as follows:

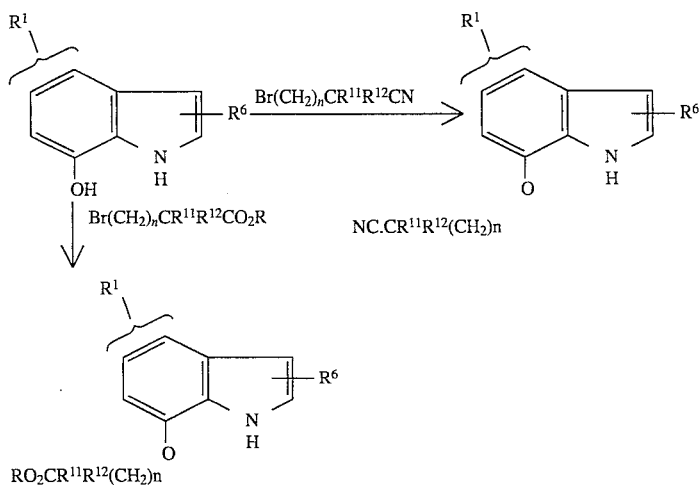

Compounds of formula (IV) in which X is attached at the 7-position can, alternatively, be prepared from a compound of formula

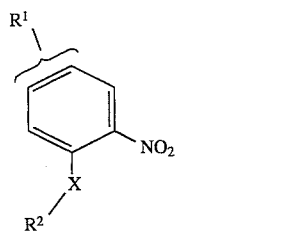

by reaction with three equivalents of vinyl Grignard reagent, or by a similar reaction on the protected ortho-nitro-phenol, protected benzaldehyde or benzoate, followed by alkylation or modification by Wittig reaction as described below. A method of making 6 carbon substituted dihydroindoles:

Compounds of formula (IV) in which X is attached at the 6-position can be prepared as follows. If it is desired to prepare intermediates of formula (IV) in which X is —$CR^{11}R^{12}$—,—$CR^{11}R^{12}(CH_2)_nCR^{13}R^{14}$— or —$CR^{11}$=$CR^{12}$—, it is convenient to start from the appropriate 6- or 7-indole carboxylate:

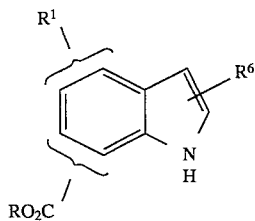

The carboxylate can be reduced with, for example, lithium aluminum hydride, to the corresponding alcohol which in its turn can be oxidized to the aldehyde with a reagent such as pyridinium dichromate, as for example:

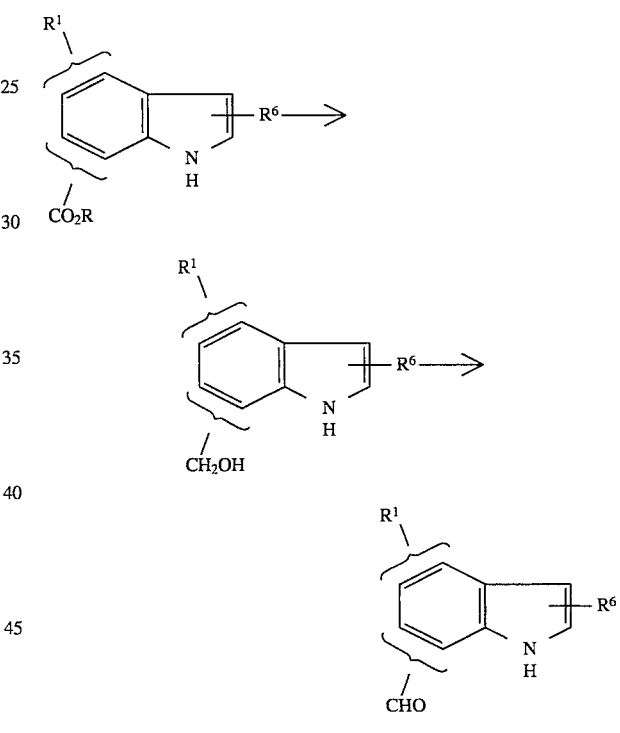

The aldehyde may be further elaborated to provide 6-substituted intermediates of formula (IV), which may then be reduced to the dihydroindole product as described above for the conversion of (10) to (11).

Alternatively, the 7-aldehyde can be synthesized by reaction of the bromo-nitrobenzene with alkenyl magnesium bromide and conversion of the bromo indole product by sodium hydride or t-butyl lithium, followed by, for example, dimethylformamide, to the aldehyde.

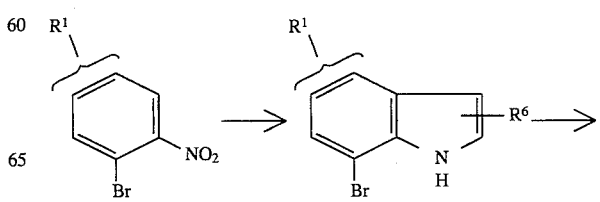

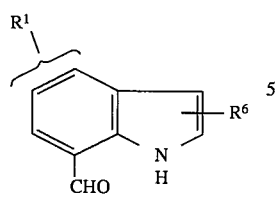

The aldehyde can then be reacted with, for example, dimethyl cyanomethyl phosphonate in the Wadsworth-Emmons reaction to give the corresponding unsaturated nitrile of formula (II) in which —X—R² is —CH=CHCN, reduction of which gives the compound in which —X—R² is —CH₂CH₂CN:

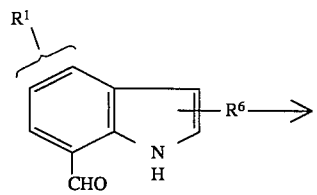

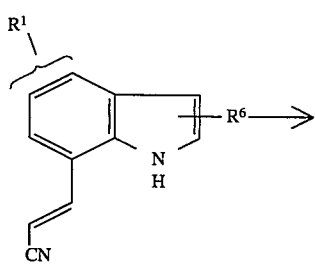

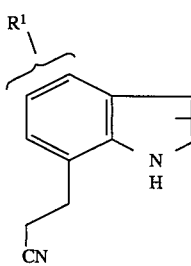

This may then be converted to the tetrazole, which can be protected with a trityl or benzyldryl group. Compounds of formula (IV) in which R² is protected tetrazolyl can also be prepared by reacting the aldehyde with an optionally protected tetrazolylmethylphosphonate prepared, for example, by reacting the appropriate amide with PCl₅ and azide.

Compounds in which R¹¹, R¹², R¹³ and R¹⁴ are other than hydrogen can be made by suitable alteration of the above synthetic routes using conventional reaction methods.

The 2,3-dihydroindole carboxylates of formula (IV)

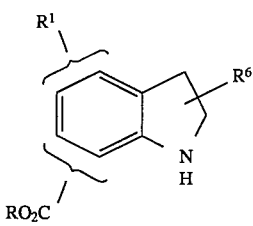

can be prepared by the Leimgruber and Batcho synthesis from the appropriate compound of formula

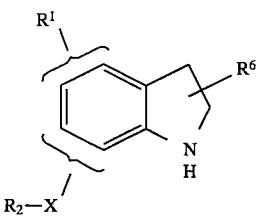

by reaction with dimethylformamide dimethyl acetal and cyclization with catalytic reduction under hydrogen over palladium on charcoal. Subsequent reduction of the indole iIntermediate with sodium cyanoborohydride in acetic acid gives the 2,3-dihydroindole. This reaction sequence can also be utilized to prepare intermediates required for the synthesis of compounds of formula (IV)

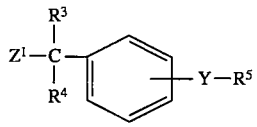

in which X is —O—(CH₂)ₙCR¹¹R¹²— attached via the oxygen atom the phenyl nucleus at the 6-position.

With regard to compounds of formula (III)

$$Z^1-\underset{R^4}{\overset{R^3}{C}}-\text{phenyl}-Y-R^5$$

these can be made by, for example, chlorination of the appropriate alcohol formed by coupling of the heterocyclic and benzene moieties, as for example, for quinolinyl derivatives:

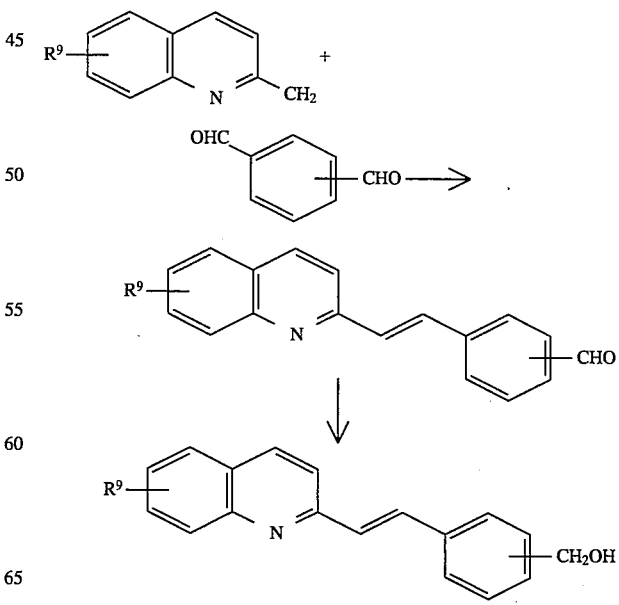

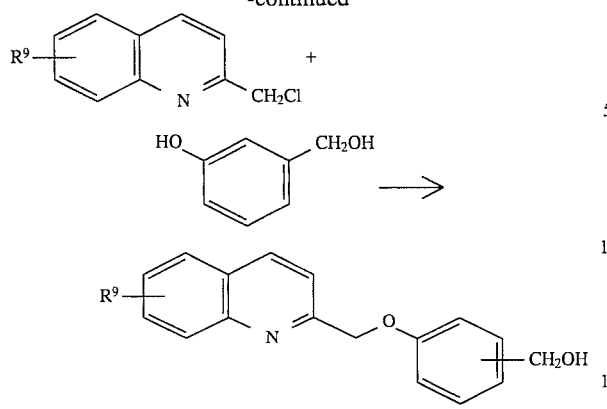

The alcohol intermediate in which $R^3$ and/or $R^4$ is other than hydrogen can be made by the reaction of Grignard reagents or alkyl or aryl lithiums on the above aldehydes, or acids for esters derived from them. In the case of compounds in which $R^3$ or $R^4$ is alkyl substituted by an acid group, the appropriate intermediate can be prepared by reaction with an acid substituted alkyl zincate. Standard methods can be employed to introduce values of $R^{15}$, $R^{16}$, $R^{17}$ and into the Y linking group between heterocycle $R^5$ and phenyl nucleus.

An alternative route to the aldehyde reactants referred to above involves the use of an appropriate phosphonium ylid which can be reacted with phenyl dialdehyde to give the desired compound. This reaction can be employed to provide the thiazolyl and pyridyl reactants of formula (III).

The compounds of formula (I) above can be prepared by alternative routes to the condensation of compounds of formulae (II) and (III), as set out above in Methods (2), (3) and (4) given above.

With regard to Method (2), this is preferably carried out in an organic solvent and in the presence of base such as for example an alkali metal hydroxide or carbonate or an alkali metal hydride, in order to effect reaction between the compounds in which $Z^3$ is —OH and $Z^2$ is —$CR^{15}R^{16}Z^1$, preferably at a temperature of from 0° C. to 150° C. The aldehyde or ketone compound in which $Z^3$ is —$CR^{15}O$ $$\overset{O}{\underset{||}{-CR^{15}}}$$

can be reacted with a compound in which $Z^2$ is methyl with acetic anhydride, optionally in an organic solvent such as for example xylene or toluene. When the reactant is of the type in which $Z^2$ is a moiety derived from an appropriate Wittig-type reagent, for example a Wittig or Wadsworth-Emmons reagent of the formula $$R^5CHR^{15}—\overset{\oplus}{P}R_3$$

$R^5CHR^{15}$—$PR_3+$ or $R^5CHR^{15}$—$P(OR)_2$ where R is an alkyl or aryl group, preferably $C_{1-4}$ alkyl or phenyl, the reaction is preferably carried out in an organic solvent in the presence of an appropriate base such as an alkali metal hydride or organo lithium compound, and at a temperature of, for example, from −70° C. to 50° C.

With regard to Method (3), this is carried out under conventional alkylation conditions, preferably at a temperature of from 0° C. to 120° C. and using an organic solvent such as for example methyl ethyl ketone, dimethylformamide, tetrahydrofuran or dimethoxyethane and in the presence of a base such as an alkali metal hydroxide or carbonate or an alkali metal hydride.

With regard to Method (4), this involves reacting a ketone or aldehyde with an isocyanide reagent of the formula $Z^1CHR^{12}$—NC where $Z^1$ is a leaving group, for example, p-toluenesulphonylmethyl isocyanide. This reaction can be performed by reacting the isocyanide with a base such as potassium tert. butoxide in a solvent such as, for example, dimethoxyethane at a temperature of, for example, −80° C. to 0° C. Alternatively, the same ketone or aldehyde compound can be reacted with an appropriate Wittig or Wadsworth-Emmons reagent of the formula $R^2CHR^{12}$—$PR_3+$ or $R^2CHR^{12}$—$P(OR)_2$, $$R^2CHR^{12}—\overset{\oplus}{P}R_3$$

$$R^2CHR^{12}—\overset{O}{\underset{||}{P}}(OR)_2,$$

under the conditions outlined for reaction (2) above.

It will be appreciated that the product of Methods (1) to (4) can be further altered by variation of one or more $R^1$, $R^2$, $R^3$ or $R^4$ group. Thus, for example, it is possible to effect the following conversions:

(i) removal of a protecting group from an acid group, such as a protected tetrazolyl or protected carboxy substituent, to give the free acid,
(ii) conversion of a nitrile group to a tetrazolyl substituent,
(iii) hydrolysis of a $C_{1-4}$ alkoxy-carbonyl group to carboxy,
(iv) conversion of a carboxy or $C_{1-4}$ alkoxy-carbonyl group to an amido group —$CONR^7R^8$, or
(v) alkylation of an amido group to provide other values of —$CONR^7R^8$.

A process for preparing a preferred group of compounds in which $R^2$ is tetrazolyl comprises removing the protecting group from a compound of formula (I) in which $R^2$ is protected tetrazolyl with, for example, acid. A further process for providing such compounds comprises reacting a compound of formula (I) in which $R^2$ is nitrile with a suitable azide, for example, tributyltin azide, optionally in an organic solvent such as for example dimethoxyethane, or an inorganic azide in dimethyl formamide, at a temperature of from 60° C. to 150° C. or 180° C., to provide a compound in which $R^2$ is tetrazolyl.

It will be appreciated that the compounds of the invention can contain one or more asymmetric carbon atoms which gives rise to isomers. The compounds are normally prepared as racemic mixtures and can conveniently be used as such but individual isomers can be isolated by conventional techniques if so desired. Such racemic mixtures and individual optical isomers form part of the present invention and it is preferred to use an enantiomerically pure form. Compounds in which one or both of the linking groups is unsaturated yield geometric isomers, and for example when Y is unsaturated the trans compounds are preferred, being the more thermally stable.

It is, of course, possible to prepare salts of the compounds of the invention and such salts are included in the invention. They can be any of the well known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicylic, o-acetoxybenzoic, or organic sulphonic, 2-hydroxyethane sulphonic, toluene-p-sulphonic, or naphthalene-2-sulphonic acid.

In addition to pharmaceutically-acceptable salts, other salts are included in the invention. They may serve as intermediates in the purification of compounds or in the preparation of other, for example pharmaceutically-acceptable, acid addition salts, or are useful for identification, characterization or purification.

Certain compounds of the invention possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters.

The compounds of the invention, excluding those in which the groups are in protected form and intermediate compounds in which $R^2$ is halo or nitrile, are pharmacologically active, being leukotriene antagonists as shown by the test of Fleisch et al. (J. Pharmacol.Exp.Ther., 233, 148–157) using the method described by Boot et al. (Br.J.Pharmacol. (1989), 98, 259–267). Isolated guinea pig ileum was suspended in Tyrode solution at 37° C. and aerated with 95% oxygen and 5% carbon dioxide. Concentration response curves to leukotriene were generated and the effects of different concentration of drug investigated. Dissociation constants ($K_B$) of the receptor-inhibitor complex were calculated by the method of Furchgott (Furchgott R. F. Handbook of Experimented Pharmacology, New York, Vol. 33 pages 383–385). The title compounds disclosed in the following Examples have a $pK_B$ of 7 to 11.

The compounds were also active in the total pulmonary resistance test (see Fleisch et al. and Boot et al., above). Measurement of bronchospasm was recorded as an increase in tracheal resistance produced by $LTD_4$ administered intravenously into anaesthetized artificially ventilated guinea pigs. The ELGV test (see, Silbaugh, S. A., et al., J. Pharm. Methods, 18: 296–303 (1987) is based on an $LTD_4$-induced bronchospasm in guinea pigs which results in increased gas trapping within the lung and the compounds of the invention prevent such gas trapping.

The compounds of the invention also antagonise $LTD_4$ radioligand binding in guinea pig lung membranes in the test described by Saussy et al., Mol. Pharmacol. 39: 72–78 1991, with a $pK_i$ of greater than 7.

The compounds of the invention are accordingly indicated for therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthmas such as Farmers lung, and in other inflammatory disorders, for example, associated with acute or chronic infectious diseases such as allergic skin diseases, ectopic and acopic eczemas, psoriasis, contact hypersensitivity and angloneurotic edema, bronchitis and cystic fibrosis and rheumatic fever.

The compounds of the invention also have potential in the treatment of vascular diseases such as shock and ischaemic heart diseases for example coronary artery disease and myocardial infarction, cerebrovascular diseases, and renal diseases, for example, renal ischemia.

Thus the invention also includes a pharmaceutical composition comprising a pharmaceutically acceptable diluent or carrier in association with a compound of formula (I) in unprotected form; or a pharmaceutically acceptable salt thereof.

The compounds may be administered by various routes, for example by the oral or rectal route, topically or parenterally, for example by injection or infusion, and especially by inhalation, being usually employed in the form of a pharmaceutical composition.

PHARMACEUTICAL COMPOSITIONS

Pharmaceutical compositions are prepared in a manner well known in the pharmaceutical art and comprise at least one Active Ingredient the term, "Active ingredient" refers to a compound of the invention). In making the compositions of the present invention, the Active Ingredient will usually be mixed with a carrier or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomizers and vaporizers.

Some examples of suitable carriers are lactose, dextrose, sucrose, sorbitol, mannitol, starches, gum acacia, calcium phosphate, alginates, cragacanth, gelatin, syrup, methyl cellulose, methyl- and propyl-, talc magnesium stearate and mineral oil. The compositions of the injection may, as is well known in the art, be formulated so as to provide quick, sustained or delayed release of the active ingredient after administration to the patent.

METHOD OF USING THE COMPOUNDS OF THE INVENTION

Where the compositions are formulated in unit dosage form, it is preferred that each unit dosage form contains from 5 mg to 500 mg, for example, from 25 mg to 200 mg. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

EXAMPLES

The invention is illustrated by the following Examples.

EXAMPLE 1

Preparation of 7-(Cyanomethoxy)indole reactant:

Part A Preparation of 2-(Benzyloxy)nitrobenzene intermediate

A stirred mixture of 2-nitrophenol (13.9 g, 0.10 mol), benzyl bromide (12.0 ml, 0.10 mol) and anhydrous potassium carbonate (30 g, 0.22 mol) in acetone (200 ml) is heated under reflux for 16 hours, cooled, poured onto ice-dilute hydrochloric acid, and extracted with dichloromethane. The extract is dried and evaporated and the residue is crystallized from ether-hexane as pale crystals, m.p. <50° C.

Part B Preparation of (Benzyloxy)-aniline intermediate

Hydrazine hydrate (5 ml) is added dropwise over 20 minutes to a stirred suspension of Raney nickel in a solution of 2-(benzyloxy)nitrobenzene in methanol (200 ml) causing gentle reflux. The stirred mixture is heated under reflux for a further 30 minutes, cooled, filtered and evaporated. The residue was distilled under vacuum to give a pale oil, b.p. 146°–150°/0.5 mm.

Part C Preparation of 2-Benzyloxy-6-(2,2-dimethoxy-1-methylthio)ethylaniline

A solution of 2-methylthioacetaldehyde dimethyl acetal (4.9 g, 36.1 mmol) in dichloromethane (10 ml) is added dropwise to a stirred solution of chlorine (2.6 g, 36.1 mmol) in dichloromethane (70 ml) at −70° C. The solution is stirred at −70° to 76° C. for 15 minutes then a solution of 2-(benzyloxy)aniline (7.2 g, 36.1 mmol) in dichloromethane (20 ml) is added over 1 hour at −70° C. The dark mixture is stirred for a further 2 hours at −70° to −75° C. then triethylamine (7 ml) is added and the mixture is allowed to warm to room temperature. After stirring for a further 1 hour, the mixture is washed successively with dilute hydrochloric acid and aqueous sodium bicarbonate solution, dried and evaporated. Chromatography of the residue on silica in ethyl acetate-hexane (1:4) gives the product contaminated with 15% of 2-(benzyloxy)aniline.

Part D Preparation of 7-(Benzyloxy)-3-(methylthio)indole intermediate

A solution of crude 2-benzyloxy-6-(2,2-dimethoxy-1-methylthio)ethylaniline (6.0 g) in ethyl acetate (100 ml) is stirred with 2M hydrochloric acid for 7 hours. The ethyl acetate layer is washed with further dilute hydrochloric acid then with sodium bicarbonate solution, dried and evaporated. The residue is chromatographed on silica in ethyl acetate-hexane (1:8) to give a pale solid.

Part E Preparation of 7-(Benzyloxy)indole intermediate

Wet Raney nickel is added in portions to a stirred refluxing solution of 7-(benzyloxy)-3-methylthio)indole (4.0 g, 14.9 mmol) in ethyl acetate (100 ml) and ethanol (60 ml) until all the starting material has been consumed (by RP HPLC). The mixture is filtered, the filtrate evaporated and the residue chromatographed on silica in ethyl acetate-hexane (1:8) to give a pale oil.

Part F Preparation of 7-(Cyanomethoxy)indole

A solution of 7-benzyloxyindole (0.5 g, 2.24 mmol) in methanol (100 ml) is hydrogenated at 60 psi (4.38 Kg/cm$^2$) over 10% palladium on charcoal (50 mg) for 4 hours. The catalyst is filtered off and the filtrate was evaporated. A stirred solution of the residue and bromoacetonitrile (0.16 ml, 2.3 mmol) in methyl ethyl ketone (5 ml) is heated under reflux with solid anhydrous potassium carbonate (0.62 g, 4.5 mmol) for 2 hours, cooled, poured onto ice-hydrochloric acid and extracted with dichloromethane. The extract is dried and evaporated and the residue is chromatographed on silica in ethyl acetate-hexane (1:2) to give a pale solid.

EXAMPLE 2

Preparation of 7-(2-Cyanoethyl)indole) starting material

Part A Preparation of Methyl 3-[2-(E)-dimethylamino)ethenyl]-2-nitro-benzoate

A solution of methyl 3-methyl-2-nitrobenzoate (43 g, 0.22 mole), dimethylformamide dimethyl acetal (52.5 g, 0.44 mole) and piperidine (18.7 g, 0.22 mole) in dimethylformamide (120 ml) is heated under reflux for 24 hours, cooled and poured into water to give the crude product.

Part B Preparation of Methyl 7-indolecarboxylate

A solution of methyl 3-[2-(E)-(dimethylamino)ethenyl]-2-nitrobenzoate (12.0 g, 48 mmol) in toluene (200 ml) is hydrogenated at 60 psi (4.22 Kg/cm$^2$) over 10% palladium on charcoal (1.5 g) until hydrogen uptake ceased. The catalyst is filtered off, the filtrate is evaporated and the residue is chromatographed on silica to give the product.

Part C Preparation of 7-Indole methanol

Solid lithium aluminum hydride (1.0 g) is added in portions over 1 hour to a stirred solution of methyl 7-indolecarboxylate (6.7 g) in tetrahydrofuran (100 ml). The mixture was stirred for a further 2 hours then excess lithium aluminum hydride was destroyed by addition of acetic acid, the mixture is diluted with aqueous sodium hydroxide and extracted with ethyl acetate. The extract is dried and evaporated and the residue is chromatographed on silica in ethyl acetate-hexane (1:9 to 1:2) to give the product.

23

Part D Preparation of 7-Indolecarboxaldehyde

Solid pyridinium dichromate (1.77 g, 5.1 mmol) is added in portions over 3 hours to a stirred solution of 7-indolemethanol (0.5 g, 3.4 mmol) in dichloromethane (50 ml). The mixture is stirred for a further 2 hours then filtered through a pad of Celite filter aid. The filtrate is evaporated and the residue purified by chromatography on silica in ethyl acetate-hexane (1:3)

Part E Preparation of 7-[2-(E)-Cyanoethenyl]indole

Sodium hydride, 60% dispersion in mineral oil (0.10 g, 2.5 mmol) is added in portions over 10 minutes to a stirred solution of diethyl cyanomethylphosphonate (0.44 g, 2.5 mmol) in tetrahydrofuran (10 ml) cooled in ice. The mixture is stirred for 15 minutes then a solution of 7-indole carboxaldehyde (0.30 g, 2.1 mmol) in tetrahydrofuran (2 ml) is added dropwise. The mixture is stirred for 30 minutes, diluted with ethyl acetate, washed with water, dried and evaporated. The residue is chromatographed on silica in ethyl acetate-hexane (1:3) to give the product.

Part F Preparation of 7-(2-Cyanoethyl)indole)

A solution of 7-[2-(E)-cyanoethyl]indole (0.28 g) in ethanol (75 ml) is hydrogenated at 50 psi (3.52 Kg/cm$^2$) over 10% palladium on charcoal (0.1 g) for 4 hours. The catalyst is filtered off and the filtrate is evaporated to give the product.

EXAMPLE 3

Preparation of 3-[2(E)-(Quinolin-2-yl)ethenyl]benzyl chloride

Part i) Methyl 3-[2(E)-(Quinolin-2-yl)ethenyl]benzoate 2.5M Butyl lithium in hexane (8.8 ml) is added over 5 minutes to a stirred solution of quinolin-2-ylmethylphosphonium chloride (9.66 g, 22 mmol) in dry tetrahydrofuran (250 ml) at −75° C. The mixture is stirred for 1 hour at −75° C. then a solution of methyl 3-formylbenzoate (3.28 g, 20 mmol) in tetrahydrofuran (25 ml) is added dropwise over 10 minutes. After stirring for a further 30 minutes at −75° C., the mixture is warmed to room temperature, diluted with water and extracted with ethyl acetate. The extract is dried and evaporated and the residue is purified by chromatography on silica eluting with ethyl acetate-hexane (1:3).

Part ii) 3-[2(E)-(Quinolin-2-yl)ethenyl]benzyl alcohol

Solid lithium aluminum hydride (025 g) is added in portions to a stirred solution of methyl 3-[2(E)-(quinolin-2-yl)ethenyl]benzoate (2.1 g, 7.3 mmol) in tetrahydrofuran (50 ml). The mixture is stirred for 30 minutes, diluted with sodium hydroxide solution and extracted with ethyl acetate. The extract is dried and evaporated and the residue chromatographed on silica in ethyl acetate-hexane.

Part iii) 3-[2(E)-Quinolin-2-yl)ethenyl]benzyl chloride

Solid N-chlorosuccinimide (0.76 g 5.72 mmol) is added in portions over 5 minutes to a stirred solution of 3-[2(E)-(quinolin-2-yl)ethenyl]benzyl alcohol (1.14 g, 4.58 mmol) and triphenylphosphine (1.50 g, 5.72 mmol) in dichloromethane (100 ml) at 0°–5° C. The mixture is stirred for a further 2 hours at 0°–5° C. then evaporated and the residue chromatographed on silica in ethyl acetate-hexane (1:3).

EXAMPLE 4

Preparation of 5-[2-[1-[3-[2-E-(7-Chloroquinolin-2-yl)ethenyl]benzyl]-2,3-dihydroindol-7-yl]-ethyl]-1H-tetrazole, a compound of the invention represented by the formula:

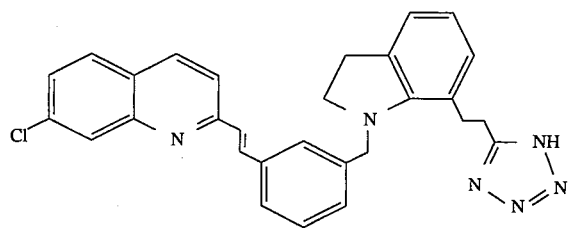

Part A. Preparation of the intermediate 7-(2-Cyanoethyl)-2,3-dihydroindole 7-(2-Cyanoethyl)indole (prepared by the method of Example 1) (8.80 g, 51.8 mmol) was suspended in acetic acid (250 mL) and treated with sodium cyanoborohydride (16.4 g, 322 mmol) at such a rate as to maintain the temperature of the reaction in the range of 10°–20° C. After addition was complete, the mixture was stirred for an additional 5 hours, diluted with water, and concentrated in vacuo. The residue was treated with 5N NaOH solution and extracted with ethyl acetate. The organic layer was washed once with water, once with saturated sodium chloride solution, dried (sodium sulfate), filtered, and concentrated in vacuo. Chromatography (Florisil®, 98% methylene chloride/2% methanol) of the resulting residue provided 8.00 g (99%) of the intermediate which crystallized upon standing.

Analysis for ($C_{11}H_{12}N_2$): Calcd: C, 76.71; H, 7.02; N, 16.27; Found: C, 76.44; H, 7.21; N, 16.52;

Part B. Preparation of the intermediate 7-(2-Cyanoethyl)-1-[3-[2-E-(7-chloroquinolin-2-yl)ethenyl]benzyl]-2,3-dihydroindole A mixture of 7-(2-cyanoethyl)-2,3-dihydroindole (690 mg, 4.01 mmol), 3-[2-E-(7-chloroquinolin-2-yl)ethenyl]benzyl chloride (produce of Example 3), 1.29 g, 4.10 mmol), and potassium carbonate (1.10 g, 7.97 mmol) in DMF (100 mL) was heated in an oil bath at 85° C. for 16 hours. The mixture was cooled and diluted with water and ethyl acetate. The organic solution was separated, washed once with water, once with saturated sodium chloride solution, then dried (over sodium sulfate), filtered and concentrated in vacuo. Chromatography (silica gel, 70% hexane/30% ether) of the resulting residue provided 850 mg (47%) of the intermediate.

Part C. Preparation of 5-[2-[1-[3-[2-E-(7-Chloroquinolin-2-yl)ethenyl]benzyl]-2,3-dihydroindol-7-yl]ethyl]-1H-tetrazole A solution of 7-(2-cyanoethyl)-1-[3-[2-E-(7-chloroquinolin-2-yl)ethenyl]benzyl]-2,3-dihydroindole (600 mg) in tri-n-butyltin azide (2.0 mL) was heated in an oil bath at 95° C. for 23 hours. To the cooled solution was added acetonitrile (50 mL), acetic acid (20 mL), and THF (10 mL). The resulting solution was stirred for 3.5 hours and washed with hexane. The hexane layer was separated and discarded. The resulting mixture was concentrated in vacuo and the residue chromatographed (silica gel, 2% methanol/98% methylene chloride) to provide a solid that was recrystallized (ethyl acetate/ether) to provide 235 mg (36%) of the desired product: mp 141°–144° C. $^1$H-NMR (DMSO-$d_6$) 8.48 (d, J=9 Hz, 1H), 8.08 (m, 2H), 7.85 (d, J=8 Hz, 1H), 7.75 (d, J=17 Hz, 1H), 7.59 (s, 1H), 7.54 (m, 2H), 7.33 (m, 3H), 7.07 (d, J=8 Hz, 1H), 6.95 (d, J=8 Hz, 1H), 6.77 (d, J=8 Hz, 1H), 4.49 (s, 2H), 3.28 (t, 2H, J=7 Hz), 3.17 (m, 2H), 3.08 (m, 2H), 2.83 (t, J=7 Hz, 2H); MS-FD m/e (493, p).

Analysis for ($C_{29}H_{25}N_6Cl$): Calcd: C, 70.65; H, 5.11; N, 17.05; Cl, 7.19 Found: C, 70.39; H, 5.17; N, 16.81; Cl, 7.45

EXAMPLE 5

Preparation of 5-[2-[1-[3-(7-Chloroquinolin-2-yl-methoxy)benzyl]-2,3-dihydroindol-7-yl]-ethyl]-1H-tetrazole, a compound of the invention represented by the formula:

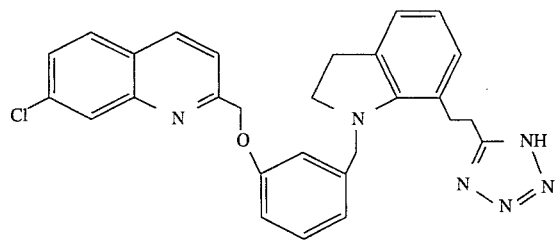

Part A. Preparation of the intermediate 7-(2-Cyanoethyl)-1-[3-(7-chloroquinolin-2-ylmethoxy)benzyl]-2,3-dihydroindole The procedure from Example 4, part B was used substituting 3-(7-chloroquinolin-2-ylmethoxy)benzyl chloride (prepared as in European Patent Appl. 0469833, Example 5) for 3-[2-E-(7-chloroquinolin-2-yl)ethenyl]benzyl chloride. The intermediate was isolated in 53% yield:

Analysis for ($C_{28}H_{24}N_3OCl$): Calcd: C, 74.08; H, 5.33; N, 9.26 Found: C, 73.82; H, 5.31; N, 9.24

Part B. 5-[2-[1-[3-(7-Chloroquinolin-2-ylmethoxy)benzyl]-2,3-dihydroindol-7-yl]-ethyl]-1H-tetrazole 7-(2-Cyanoethyl)-1-[3-(7-chloroquinolin-2-ylmethoxy)benzyl]-2,3-dihydroindole was reacted as described in Example 4, part C to give the product in 40% yield as a tan solid: mp 137°–140° C.

Analysis for ($C_{28}H_{25}N_6OCl$): Calcd: C, 67.67; H, 5.07; N, 16.91 Found: C, 67.96; H, 5.14; N, 16.69

EXAMPLE 6

Preparation of 5-[2-[1-[4-(7-Chloroquinolin-2-yl-methoxy)benzyl]-2,3-dihydroindol-7-yl]-ethyl]-1H-tetrazole, compound of the invention represented by the formula:

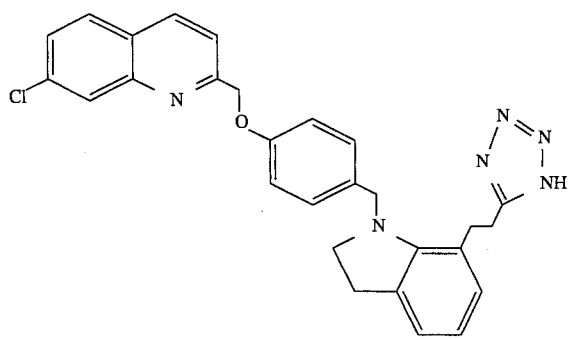

Part A. Preparation of the intermediate 4-(7-Chloroquinolin-2-ylmethoxy)benzyl alcohol A solution of 4-hydroxybenzyl alcohol (2.70 g, 21.8 mmol) in DMF (50 mL) was treated with sodium hydride (0.666 g, 27.8 mmol) at room temperature. After gas evolution had ceased, 7-chloro(2-chloromethyl)quinoline (4.20 g, 19.8 mmol) was added and the resulting mixture stirred for 4 hours. The mixture was diluted with water and extracted with ethyl acetate. The organic layer was washed thrice with water, dried (sodium sulfate), filtered, and concentrated in vacuo. The residue was triturated with 5% ethyl acetate/95% hexane and filtered to provide 5.90 g of the intermediate (99%).

Analysis for ($C_{17}H_{14}NO_2Cl$): Calcd: C, 68.12; H, 4.71; N, 4.67 Found: C, 68.76; H, 5.39; N, 4.56

Part B. Preparation of the intermediate 4-(7-Chloroquinolin-2-ylmethoxy)benzyl chloride A mixture of 4-(7-chloroquinolin-2-ylmethoxy)benzyl alcohol (2.80 g, 9.33 mmol), triethylamine (3.12 g, 30.9 mmol), lithium chloride (0.850 g, 20.0 mmol), and 4-(N,N-dimethylamino)pyridine (10 mg) in DMF (40 mL) was cooled to −10° C. Methanesulfonyl chloride (3.40 g, 29.7 mmol) was added dropwise and the resulting mixture was stirred for 15 minutes. The mixture was warmed to room temperature and stirred for an additional 4 hours, then diluted with ethyl acetate. The resulting solution was washed once with water, dried (sodium sulfate), filtered, and concentrated in vacuo. Chromatography of the residue (silica gel, ethyl acetate/hexane gradient) provided 1.60 g (54%) of the intermediate.

Part C. Preparation of the intermediate 7-(2-Cyanoethyl)-1-[4-(7-chloroquinolin-2-ylmethoxy)benzyl]-2,3-dihydroindole The procedure from Example 4, Part B was used substituting 4-(7-chloroquinolin-2-ylmethoxy)benzyl chloride for 3-[2-E-(7-chloroquinolin-2-yl)ethenyl]benzyl chloride. The intermediate was isolated in 64% yield.

Analysis for ($C_{28}H_{24}N_3OCl$): Calcd: C, 74.08; H, 5.33; N, 9.26 Found: C, 74.29; H, 5.40; N, 9.35

Part D. Preparation of the product, 5-[2-[1-[4-(7-chloroquinolin-2-ylmethoxy)benzyl]-2,3-dihydroindol-7-yl]-ethyl]-1H-tetrazole 7-(2-Cyanoethyl)-1-[4-(7-chloroquinolin-2-ylmethoxy)benzyl]-2,3-dihydroindole was reacted as described in Example 4, part C to provide the product in 43% yield as an off-white solid: mp 69°–73° C. $^1$H-NMR (DMSO-$d_6$) 8.48 (d, J=9 Hz, 1H), 8.07 (s, 1H), 8.05 (d, J=9 Hz, 1H), 7.72 (d, J=9 Hz, 1H), 7.68 (dd, J=9, 1 Hz, 1H), 7.24 (d, J=9 Hz, 2H), 7.02 (d, J=9 Hz, 2H), 6.95 (d, J=8 Hz, 1H), 6.83 (d, J=8 Hz, 1H), 6.63 (C, J=8 Hz, 1H), 5.34 (s, 2H), 4.26 (s, 2H), 3.22 (t, J=7 Hz, 2H), 3.18 (m, 2H), 3.09 (m, 2H), 2.84 (t, J=7 Hz, 2H); MS-FD m/e (497, p).

Analysis for ($C_{28}H_{25}N_6OCl$): Calcd: C, 67.67; H, 5.07; N, 16.91 Found: C, 67.9 0; H, 5.2 6; N, 16.97

EXAMPLE 7

Preparation of 5-[2-[1-[3-(Quinolin-2-ylmethoxy)benzyl]-2,3-dihydroindol-7-yl]-ethyl]-1H-tetrazole, a compound represented by the formula:

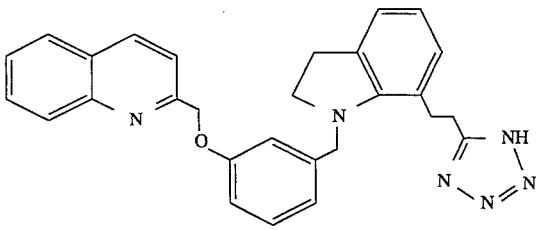

Part A. Preparation of the intermediate 2-(Quinolin-2-ylmethoxy)benzyl alcohol

The procedure from Example 6, part A was used except 2-(chloromethyl)quinoline was substituted for 7-chloro(2-chloromethyl)quinoline and 3-hydroxybenzyl alcohol was substituted for 4-hydroxybenzyl alcohol. The intermediate was obtained in 85% yield: mp 82°–86° C.

Analysis for ($C_{17}H_{15}NO_2$): Calcd: C, 76.96; H, 5.70; N, 5.28 Found: C, 76.97; H. 5.76; N. 5.53

Part B. Preparation of the intermediate 3-(Quinolin-2-ylmethoxy)benzyl chloride

The procedure from Example 6, part B was used except 3-(quinolin-2-ylmethoxy)benzyl alcohol was substituted for 4-(7-chloroquinolin-2-ylmethoxy)benzyl alcohol. The intermediate was obtained in 72% yield: mp 39°–43° C.

Part C. Preparation of the intermediate 7-(2-Cyanoethyl)-1-[3-(quinolin-2-ylmethoxy)benzyl]-2,3-dihydroindole The procedure from Example 4, part B was used substituting 3-(quinolin-2-ylmethoxy)benzyl chloride for 3-[2-E-(7-chloroquinolin-2-yl)ethenyl]benzyl chloride. The intermediate was isolated in 49% yield.

Part D. Preparation of the product 5-[2-[1-[3-(Quinolin-2-ylmethoxy)benzyl]-2,3-dihydroindol-7-yl]ethyl]-1H-tetrazole 7-(2-Cyanoethyl)-1-[3-(quinolin-2-ylmethoxy)benzyl]-2,3-dihydroindole was reacted as described in Example 4, pare C to provide the product in 16% yield as an off-white solid: mp 148°–151° C. $^1$H-NMR (DMSO-$d_6$) 8.40 (d, J=9 Hz, 1H), 7.98 (m, 2H), 7.77 (t, J=8 Hz, 1H), 7.64 (m, 2H), 7.44 (t, J=8 Hz, 1H), 7.04 (s, 1H), 6.93 (m, 3H), 6.82 (d, J=8 Hz, 1H), 6.64 (t, J=8 Hz, 1H), 5.34 (s, 2H), 4.35 (s, 2H), 3.24 (t, J=8 Hz, 2H), 3.15 (m, 2H), 3.06 (m, 2H), 2.83 (t, J=8 Hz, 2H); MS-FD m/e (462, p).

Analysis for ($C_{28}H_{26}N_6O$): Calcd: C, 72.71; H, 5.67; N, 18.17 Found: C, 72.48; H, 5.46; N, 18.16

EXAMPLE 8

Preparation of 5-[2-[1-[4-(Quinolin-2-ylmethoxy)benzyl]-2,3-dihydroindol-7-yl]-ethyl]-1H-tetrazole, a compound of this invention represented by the formula:

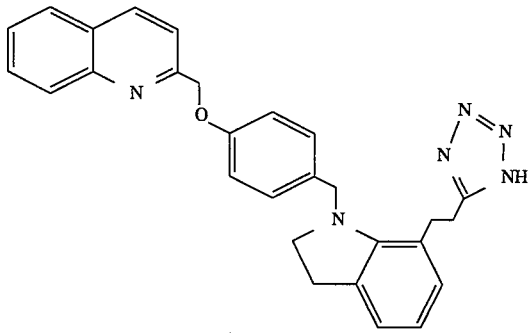

Part A. Preparation of the intermediate 4- Quinolin-2-ylmethoxy)benzyl alcohol

The procedure from Example 6, part A was used except 2-(chloromethyl)quinoline was substituted for 7-chloro(2-chloromethyl)quinoline. The crude material was triturated with 5% ethyl acetate/95% hexane to provide the intermediate in 78% yield: mp 131°–135° C.

Part B. Preparation of the intermediate 4-(Quinolin-2-ylmethoxy)benzyl chloride

The procedure from Example 6, part B was used except 4-(quinolin-2-ylmethoxy)benzyl alcohol was substituted for 4-(7-chloroquinolin-2-ylmethoxy)benzyl alcohol. The intermediate was obtained in 47% yield.

Part C. Preparation of the intermediate 7-(2-Cyanoethyl)-1-[4-(quinolin-2-ylmethoxy)benzyl]-2,3-dihydroindole The procedure from Example 4, part B was used substituting 4-(quinolin-2-ylmethoxy)benzyl chloride for 3-[2-E-(7-chloroquinolin-2-yl)ethenyl]benzyl chloride. The intermediate was isolated in 58% yield.

Part D. Preparation of the product, 5-[2-[1-[4-(Quinolin-2-ylmethoxy)benzyl]-2,3-dihydroindol-7-yl]ethyl]-1H-tetrazole 7-(2-Cyanoethyl)-1-[4-(quinolin-2-ylmethoxy)benzyl]-2,3-dihydroindole was reacted as described in Example 4, part C to provide the product in 7% yield as an off-white solid: mp 64°–67° C. $^1$H—NMR (DMSO-$d_6$) 8.42 (d, J=9 Hz, 1H), 8.02 (m, 2H), 7.77 (t, J=8 Hz, 1H), 7.67 (d, J=9 Hz, 1H), 7.63 (t, J=8 Hz, 1H), 7.23 (d, J=9 Hz, 2H), 7.02 (d, J=9 Hz, 2H), 6.94 (d, J=8 Hz, 1H), 6.83 (d, J=8 Hz, 1H), 6.63 (t, J=8 Hz, 1H), 5.34 (S, 2H), 4.29 (s, 2H), 3.21 (t, J=7 Hz, 2H), 3.17 (m, 2H), 3.08 (m, 2H), 2.82 (t, J=7 Hz, 2H); MS-FD m/e (462, p).

Analysis for ($C_{28}H_{26}N_6O$·0.25 EtOAc): Calcd: C, 71.88; H, 5.82; N, 17.34 Found: C, 71.83; H, 5.57; N, 17.26

EXAMPLE 9

Preparation of 5-[2-[1-[3-[2-E-(Quinolin-2-yl)ethenyl]benzyl]-2,3-dihydroindol-7-yl]ethyl]-1H-tetrazole, a compound of this invention represented by the formula:

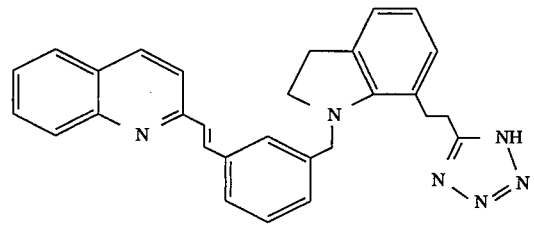

Part A. Preparation of the intermediate 7-(2-Cyanoethyl)-1-[3-[2-E-(quinolin-2-yl)ethenyl]benzyl]-2,3-dihydroindole The procedure from Example 4, part B was used substituting 3-[2-E-(quinolin-2-yl)ethenyl]benzyl chloride for 3-[2-E-(7-chloroquinolin-2-yl)ethenyl]benzyl chloride. The intermediate was isolated in 56% yield: mp 126°–129° C.

Analysis for ($C_{29}H_{25}N_3$): Calcd: C, 83.82; H, 6.06; N, 10.11 Found: C, 83.58; H, 6.22; N, 10.09

Part B Preparation of the intermediate 5-[2-[1-[3-[2-E-(Quinolin-2-yl)ethenyl]benzyl]-2,3-dihydroindol-7-yl]-ethyl]-1H-tetrazole 7-(2-Cyanoethyl)-1-[3-[2-E-(quinolin-2-yl)ethenyl]benzyl]-2,3-dihydroindole was reacted as described in Example 4, part C to provide the intermediate in 43% yield: mp 76°–82° C. $^1$H-NMR (DMSO-$d_6$) 8.35 J=9 Hz, 1H), 7.97 (m, 2H), 7.89 (d, J=9 Hz, 1H), 7.84 J=16 Hz, 1H), 7.75 (m, 2H), 7.63 (d, J=8 Hz, 1H), 7.57 (t, J=8 Hz, 1H), 7.48 (d, J=16 Hz, 1H), 7.40 (t, J=8 Hz, 1H), 7.33 (d, J=8 Hz, 1H), 7.00 (d, J=8 Hz, 1H), 6.88 (d, J=8 Hz, 1H), 6.69 (t, J=8 Hz, 1H), 4.42 (s, 2H), 3.35 (t, J=7 Hz, 2H), 3.18 (m, 2H), 3.11 (m, 2H), 2.91 (t, J=7 Hz, 2H); MS-FD m/e (458, p).

Analysis for ($C_{29}H_{26}N_6$·1.6 MeOH): Calcd: C, 72.09; H, 6.23; N, 16.48 Found: C, 72.36; H, 6.03; N, 16.08

EXAMPLE 10

Preparation of 5-[1-[3-[2-E-(7-Chloroquinolin-2-yl)ethenyl]benzyl]-2,3-dihydroindol-7-yloxymethyl]-1H-tetrazole, a compound of the invention represented by the formula:

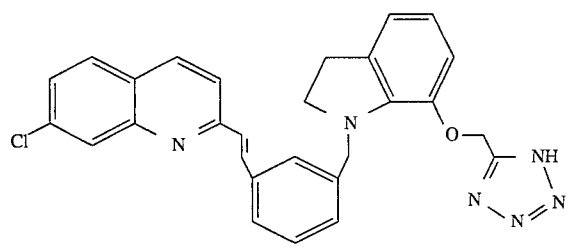

Part A. Preparation of the intermediate 7-(Cyanomethoxy)-2,3-dihydroindole 7-(Cyanomethoxy)indole (product of Example 1) was reduced according to the procedure described in Example 4, part A to provide the intermediate in 90% yield.

Part B. Preparation of the intermediate 1-[3-[2-E-(7-Chloroquinolin-2-yl)ethenyl]benzyl]-2,3-dihydroindol-7-yloxyacetonitrile The procedure from Example 4, part B was used substituting 7-(cyanomethoxy)-2,3-dihydroindole for 7-(2-cyanoethyl)-2,3-dihydroindole. The intermediate was isolated in 52% yield.

Part C. Preparation of the product 5-[1-[3-[2-E-(7-Chloroquinolin-2-yl)ethenyl]benzyl]-2,3-dihydroindol-7-yloxymethyl]-1H-tetrazole 1-[3-[2-E-(7-Chloroquinolin-2-yl)ethenyl]benzyl]-2,3-dihydroindol-7-yloxyacetonitrile was reacted as described in Example 4, part C to provide the product in 16% yield: mp 188°–191° C. $^1$H-NMR (DMSO-$d_6$) 8.41 (d, J=9 Hz, 1H), 8.02 (m, 2H), 7.94 (d, J=8 Hz, 1H), 7.83 (d, J=17 Hz, 1H), 7.61 (m, 3H), 7.43 (d, J=17 Hz, 1H), 7.35 (t, J=8 Hz, 1H), 7.26 (d, J=8 Hz, 1H), 6.90 (d, J=9 Hz, 1H), 6.88 (d, J=7 Hz, 1H), 6.64 (t, J=8 Hz, 1H), 5.46 (s, 2H), 4.58 (s, 2H), 3.23 (t, J=7 Hz, 2H), 2.88 (t, J=7 Hz, 2H); MS-FD m/e (494, p).

Analysis for ($C_{28}H_{23}N_6OCl$): Calcd: C, 67.94; H, 4.68; N, 16.98 Found: C, 67.65; H, 4.69; N, 16.94

EXAMPLE 11

Preparation of 5-[2-[1-[4-[2-E-(7-Chloroquinolin-2-yl)ethenyl]benzyl]-2,3-dihydroindol-7-yl]-ethyl]-1H-tetrazole, a compound of the invention represented by the formula:

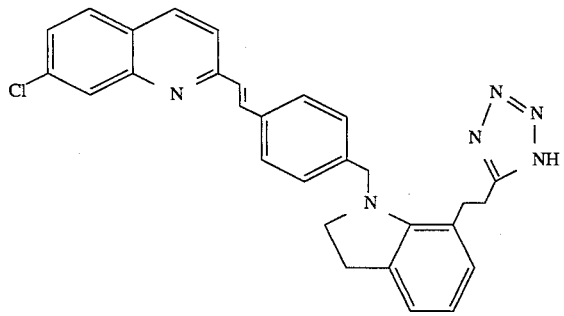

Part A. Preparation of the intermediate 7-(2-Cyanoethyl)-1-[4-[2-E-(7-chloroquinolin-2-yl)ethenyl]benzyl]-2,3-dihydroindole The procedure from Example 4, part B was used substituting 4-[2-E-(7-chloroquinolin-2-yl)ethenyl]benzyl chloride (product of Example 3) for 3-[2-E-(7-chloroquinolin-2-yl)ethenyl]benzyl chloride. The intermediate was isolated in 41% yield.

Analysis for ($C_{29}H_{24}N_3Cl$): Calcd: C, 77.41; H, 5.38; N, 9.34 Found: C, 77.70; H, 5.32; N, 9.38

Part B. Preparation of the product, 5-[2-[1-[4-[2-E-(7-Chloroquinolin-2-yl)ethenyl]benzyl]-2,3-dihydroindol-7-yl]ethyl]-1H-tetrazole 7-(2-Cyanoethyl)-1-[4-[2-E-(7-chloroquinolin-2-yl)ethenyl]benzyl]-2,3-dihydroindole was reacted as described in Example 4, part C to provide the product in 47% yield: mp 83°–87° C. $^1$H-NMR (DMSO-$d_6$) 8.41 (d, J=8 Hz, 1H), 8.00 (m, 2H), 7.90 (d, J=8 Hz, 1H), 7.84 (d, J=18 Hz, 1H), 7.73 (d, J=9 Hz, 2H), 7.59 (dd, J=8, 1 Hz, 1H), 7.47 (d, J=17 Hz, 1H), 7.39 (d, J=9 Hz, 2H), 6.98 (d, J=8 Hz, 1H), 6.86 (d, J=8 Hz, 1H), 6.65 (t, J=8 Hz, 1H), 4.41 (s, 2H), 3.32 (t, J=7 Hz, 2H), 3.18 (m, 2H), 3.11 (m, 2H), 2.90 (t, J=7 Hz, 2H); MS-FD m/e (493, p).

Analysis for ($C_{29}H_{25}N_6Cl$): Calcd: C, 70.65; H, 5.11; N, 17.05 Found: C, 70.40; H, 5.10; N, 16.76

ASSAY METHODS

Assay 1—Guinea Pig Tracheae

Leukotriene receptor antagonism was evaluated in isolated smooth muscles by the following procedure:

Male Hartley guinea pigs weighing 250–400 grams were asphyxiated with $CO_2$ and exsanguinated. Trachea were excised and placed in Krebs'-bicarbonate solution of the following composition in mM/liter: NaCl, 118.2; $NaHCO_3$, 24.8; KCl, 4.6; $KH_2PO_4$, 1.2, $MgSO_4.7H_2O$, 1.2; dextrose, 10.0; $CaCl_2.2H_2O$, 2.5; l-cysteine, 3.0, and indomethacin, 3 μM. Trachea were cut into ring segments and the epithelium removed by gently rubbing the luminal surface with a cotton swab. Tracheal rings were placed on supports constructed from two 1 inch 30 gauge disposable stainless steel hypodermic needles (Hooker, et al., 1977, Blood Vessels 14: 1–11), and transferred to organ baths containing Krebs' solution maintained at 37° C. and aerated with 95% $O_2$ and 5% $CO_2$. Isometric measurements were made with a Grass FTO3C force-displacement transducer and recorded on a Grass polygraph as changes in grams of force. After approximately 60 minutes of equilibration, a single submaximal concentration of $LTD_4$ ($3\times10^{-8}$M) was used to contract the trachea. Two $LTD_4$ concentration-response curves were then generated using the cumulative response technique of Van Rossum (1963). A potential leukotriene receptor antagonist was as added to the tissue bath 45 minutes prior to generation of the second $LTD_4$ concentration-response curve.

Assay 2—Guinea Pig Ileum

Guinea pig ileum was used to determine the potency of novel $LTD_4$ receptor antagonists on intestinal smooth muscle receptors. Terminal ilea were removed from the animals exsanguinated after $CO_2$ asphyxiation and cut into smaller segments of approximately 2 to 3 cm. Tissues were placed in organ baths containing Krebs' bicarbonate solution prepared without indomethacin and 1-cysteine and aerated with 95% $O_2$ and 5% $CO_2$. After a 60 minute equilibration period, 3 submaximal contractions to histamine ($3\times10^{-6}$M) were obtained on all tissues. A cumulative concentration-response curve to $LTD_4$ was then generated using the method of Van Rossum (Arch. Int. Pharmacodyn. Ther. 143: 299, 1963). Agonist was washed from the baths and the tissues permitted to recover. After a second $LTD_4$ concentration-response curve was produced, the ilea were washed once again and permitted to re-equilibrate. Experimental drug was added to the baths 30 minutes prior to a final $LTD_4$ concentration-response curve.

The contractions of trachea and ilea to $LTD_4$ in the presence of the drug was compared to responses in the absence of drug. $K_B$ values were calculated by the method of Furchgott (Ann. N.Y. Acad. Sci., 139:553, 1967) using the following equation: $K_B$=[Antagonist]/Dose-Ratio-1. Dose-ratio refers to the concentration of agonist required to elicit 50% of the maximal response ($ED_{50}$) in the presence of the antagonist divided by the ED50 in the absence of the antagonist.

Assay 3—Guinea Pig Lung Membrane [$^3$H] LTD$_4$Radioligand Binding

[3H] LTD$_4$ was purchased from New England Nuclear (Boston, Mass.). All other chemicals were purchased from Sigma (St. Louis, Mo.).

Incubations were performed in silanised glass tubes and contained 30 mg of guinea-pig lung membrane preparation (Saussy, et al., *Mol. Pharmacol.* 39: 72–78, 1991), in a buffer consisting of 25 mM MOPS, 10 mM L-cysteine, 10 mM glycine, 10 mM CaCl$_2$, 10 mM MgCl$_2$ adjusted to pH 6.5, 50 ml vehicle or non specific LTD$_4$ (1 mM) or displacing compound and 250 ml tracer 58,000–80,000 dpm) [$^3$H] LTD$_4$ 128–168 Ci/mmol in assay buffer. The binding reaction was terminated after 30 min. at 30° C. by the addition of 4 ml ice cold wash buffer (25 mM Tris —HCl, pH 7.5), followed immediately by vacuum filtration over Whatman (GF/C glass fibre filters, using a Brandel (Gaithersburg, Md.) 48 place harvester. The tubes and filter were washed 3×4 ml in cold wash buffer. Retained radioactivity was determined by liquid scintillation counting at 50% counting efficiency using Ready Protein Plus cocktail (Beckman, Fullerton, Calif.). Data were analyzed using linear regression analysis of log-logit plots of the values between 10% and 90% of control hiding to calculate IC$_{50s}$ and slope factors (pseudo-Hill coefficients). IC$_{50}$ values were corrected for radioligand concentrations (Cheng and Prusoff, *Biochem. Pharmacol.* 22: 3099–3108, 1973) to calculate K$_i$ values.

Airway obstruction (excised lung gas volume) Guinea pigs were dosed orally with the test compound 2 or 6 hours prior to an LTD$_4$ aerosol challenge. For aerosol challenge, animals were placed in plastic restraint tubes, connected to a nose only inhalation exposure chamber and exposed for 8 minutes to a 3.0 mg/ml solution concentration. At the end of the challenge, animals were killed with a 2.0 ml intraperitoneal injection of a euthanasia solution. At death, the abdomen of each guinea pig was quickly opened, the diaphragm punctured, and the lungs allowed to passively deflate. The lungs were then removed and attached via the trachea to a brass weight. The magnitude of airway obstruction was then quantitated by determination of the amount of gas trapped within the lung. Excised lung gas volumes (ELGV) were determined by immersing the lungs plus weight in saline and measuring buoyancy effects on an analytical balance (Silbaugh, S. A., et al., 1987, Pulmonary gas trapping in the guinea pig and its application in pharmacological testing. *J. Pharmacol. Methods,* 18: 296–303.)

The meshing of the compounds of Formula I in these procedures in summarized in Table I.

TABLE I

| Example No | GPLM binding[1] (pK$_i$) | GP ileum[2] (pK$_b$) | GP trach[3] (pK$_b$) |
|---|---|---|---|
| 4 | 8.3 | 8.63 | 7.54 |
| 5 | 8.0 | 8.41 | 8.08 |
| 6 | 7.6 | 8.49 | 7.59 |
| 7 | 7.3 | 7.95 | 7.80 |
| 8 | 7.8 | 8.26 | 8.41 |
| 9 | 7.8 | 8.60 | NT |
| 10 | 8.61 | NT | NT |
| 11 | 8.63 | NT | NT |

Note:
NT is not tested.
[1]is binding by Assay Method 1, supra.
[2]is ileum by Assay Method 2, supra.
[3]is trach by Assay Method 3, supra.

The compounds or formulations of the present invention may be administered by the oral and rectal routes, topically, parenterally, e.g. by injection or by continuous or discontinuous intra-arterial infusion, in the form of for example, tablets, lozenges, sublingual tablets, suspensions, aerosols, ointments, for example, containing from 0.1 to 10% by weight of the active compound in a suitable base, gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 1 to 500 mg. of a compound of Formula I. Dosages of from about 0.1 to 300 mg/kg. of active ingredient may be adminsitered although it will, of course, readily be understood that the amount of the compound or compounds of formula I actually to be administered will be determined by a physician, in the light of all the relevant circumstances inclusing the condition to be treated, the choice of compound to be administered and the choice of route of administration and thererfore the above preferred dosage range is not intended to limit the scope of the present invention in any way.

The formulations of the present invention normally will consist of at least one compound of formula I mixed with a carrier or diluted by a carrier, A carrier or diluent may be a solid, semi-solid, or liquid material which serves as a vehicle, excipient or medium of the active therapeutic substance.

Some examples of the diluents or carrier which may be employed in the pharmaceutical compositions of the present invention are lactose, dextrose, sucrose, sorbitol, mannitol, propylene glycol, fumed silicon dioxide, microcrystalline cellulose, calcium silicate, silica, polyvinylpyrrolidone, starch, modified starches, gum acacia, calcium phosphate, cocoa butter, ethoxylated esters, oil alginates, gelatin, methyl cellulose, polyoxytheylene sorbitan monolaurate, ethyl lactate, methyl and propyl hydroxybenzoate, sorbitan trioleate, sorbitan sesquioleate. In the case of tablets, a lubricant may be incorporated to prevent sticking and binding of the powdered ingredients in the die and on the punch of the tableting machine. For such purpose there may be employed for instance aluminum, magnesium of calcium stearates, talc or mineral oil.

I claim:

1. A compound of formula (I) or a pharmaceutically acceptable salt thereof;

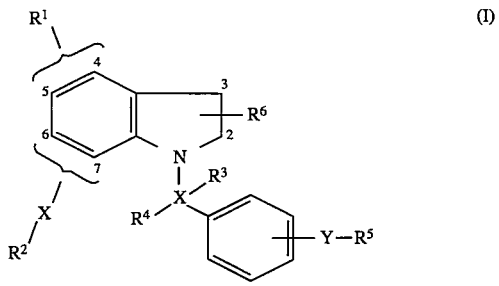

wherein $R^1$ is hydrogen, halo, $C_{1-4}$ alkyl, $C_{1-4}$ alkoxy, nitrile, optionally protected carboxy, optionally protected tetrazolyl, trihalomethyl, hydroxy-$C_{1-4}$ alkyl, aldehydo, —CH$_2$Z, —CH=CH—Z or —CH$_2$CH$_2$Z, where Z is optionally protected carboxy or optionally protected tetrazolyl;

$R^2$ is halo, nitrile, an optionally protected acid group, $C_{1-4}$ alkoxy-carbonyl, or —CONR$^7$R$^8$ where R$^7$ and R$^8$ are each hydrogen or $C_{1-4}$ alkyl;

$R^3$ and $R^4$ are each hydrogen, $C_{1-4}$ alkyl, optionally substituted phenyl, or $C_{1-4}$ alkyl substituted by —CONR$^7$R$^8$ or an optionally protected acid group;

$R^5$ is selected from the following three formulae:

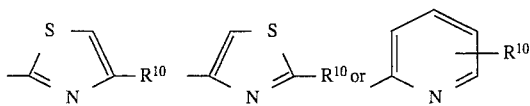

where $R^{10}$ is hydrogen, $C_{1-4}$ alkyl, $C_{2-6}$ alkenyl, $C_{3-6}$ cycloalkyl or $C_{1-4}$ alkyl-$C_{3-6}$ cycloalkyl; $R^6$ is hydrogen or $C_{1-4}$ alkyl;

each X is independently selected from, $-O-(CH_2)_n-CR^{11}R^{12}-$, $-S-(CH_2)_n-CR^{11}R^{12}-$, $-CR^{11}R^{12}-$, $-CR^{11}R^{12}-(CH_2)_n-CR^{13}R^{14}-$ or $-CR^{11}=CR^{12}-$, where $R^{11}, R^{12}, R^{13}$ and $R^{14}$ are each hydrogen or $C_{1-4}$ alkyl;

n is 0, 1 or 2; and

Y is $-O-CR^{15}R^{16}-$, $-S-CR^{15}R^{16}-$, $-CR^{15}=CR^{16}-$ or $-CR^{15}R^{16}-CR^{17}R^{18}-$ where $R^{15}, R^{16}, R^{17}$ and $R^{18}$ are each hydrogen or $C_{1-4}$ alkyl.

2. The compound of claim 1 wherein $R^1$ is selected from hydrogen or halogen.

3. The compound of claim 1 wherein the $R^2$ is an acid group selected from tetrazolyl and carboxy.

4. The compound of claim 1 wherein $R^3$ and $R^4$ are selected from the groups (i), (ii) or (iii) where;

(i) $R^3$ and $R^4$ are independently selected from hydrogen, $C_{1-4}$ alkyl, and substituted phenyl;

(ii) $R^3$ and $R^4$ are both hydrogen, $R^3$ is hydrogen and $R^4$ is $C_{1-4}$ alkyl or optionally substituted phenyl, or $R^3$ and $R^4$ are each $C_{1-4}$ alkyl; and (iii) $R^3$ is $C_{1-4}$ alkyl substituted by an acid group and $R^4$ is hydrogen or $C_{1-4}$ alkyl.

5. The compound of claim 1 wherein $R^6$ is selected from hydrogen and $C_{1-4}$ alkyl, with the proviso that when $R^6$ is $C_{1-4}$ alkyl it is attached at the 3-position.

6. The compound of claim 1 wherein X is $-O-CR^{11}R^{12}-$ or $CR^{11}R^{12}-CR^{13}R^{14}-$, and $R^{11}, R^{12}, R^{13}$ and $R^{14}$ are hydrogen.

7. The compound of claim 1 wherein linking group Y is $-O-CR^{15}R^{16}-$ or $-CR^{15}=CR^{16}-$, and $R^{15}, R^{16}, R^{17}$ and $R^{18}$ are hydrogen.

* * * * *